United States Patent [19]

Magnussen et al.

[11] 4,163,027
[45] Jul. 31, 1979

[54] WORKING-UP OF REACTION MIXTURES CONTAINING CYCLOHEXANOL AND CYCLOHEXANONE

[75] Inventors: Peter Magnussen, Bad Duerkheim; Guenter Herrmann, Neustadt; Elmar Frommer, Ludwigshafen, all of Fed. Rep. of Germany

[73] Assignee: BASF Aktiengesellschaft, Fed. Rep. of Germany

[21] Appl. No.: 844,985

[22] Filed: Oct. 25, 1977

[30] Foreign Application Priority Data

Nov. 6, 1976 [DE] Fed. Rep. of Germany ....... 2650892
Oct. 8, 1977 [DE] Fed. Rep. of Germany ....... 2745448

[51] Int. Cl.² .................. C07C 27/12; C07C 27/26; C07C 29/24; C07C 45/24
[52] U.S. Cl. ..................... 260/586 P; 260/586 R; 568/836
[58] Field of Search .......... 260/586 P, 586 R; 568/836

[56] References Cited

U.S. PATENT DOCUMENTS

| 2,931,834 | 4/1960 | Crouch et al. | 260/586 P |
| 2,938,924 | 5/1960 | Simon et al. | 260/586 P |
| 3,439,041 | 4/1969 | Gey et al. | 568/836 |
| 3,551,482 | 12/1970 | Gey et al. | 260/586 P |
| 3,946,077 | 3/1976 | Thiel et al. | 260/586 P |

FOREIGN PATENT DOCUMENTS

| 1046610 | 6/1959 | Fed. Rep. of Germany . | |
| 49-48309 | 11/1970 | Japan | 260/586 P |
| 7004497 | 9/1971 | Netherlands | 260/586 P |
| 7207532 | 12/1972 | Netherlands | 260/586 P |

Primary Examiner—Norman Morgenstern
Attorney, Agent, or Firm—Keil & Witherspoon

[57] ABSTRACT

A process for working up reaction mixtures containing cyclohexanol and cyclohexanone, which have been obtained by oxidizing cyclohexane with molecular oxygen or gases containing molecular oxygen, in the liquid phase, at from 130° to 200° C. under a pressure of from 5 to 25 bars, working-up being effected by treatment with aqueous solutions of an alkali metal hydroxide and/or alkali metal carbonate in two stages, the fresh aqueous alkali metal hydroxide and/or alkali metal carbonate solution being fed to the second stage and the separated-off spent alkali being brought into contact with fresh reaction mixture in the first stage. The treatment in the first stage is carried out in the presence of inert gases and the inert gases are separated off before the second stage.

9 Claims, 1 Drawing Figure

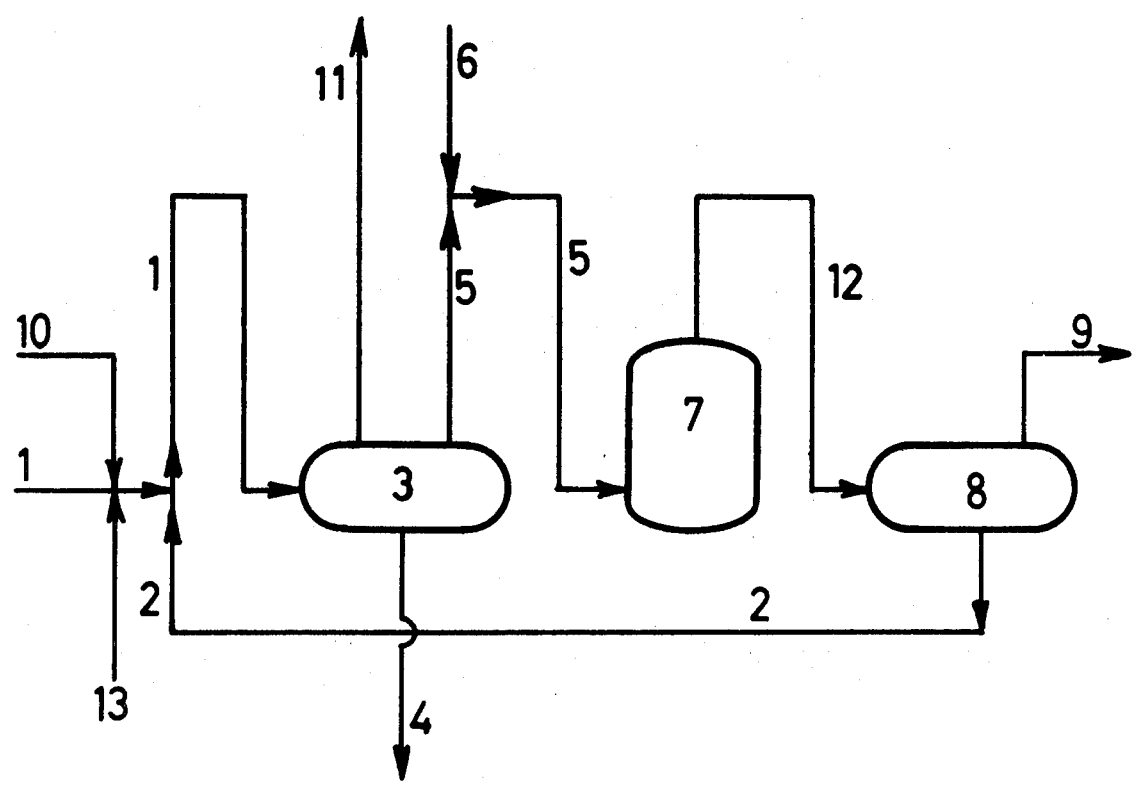

WORKING-UP OF REACTION MIXTURES CONTAINING CYCLOHEXANOL AND CYCLOHEXANONE

The present invention relates to a process for working up reaction mixtures containing cyclohexanol and cyclohexanone, which have been obtained by oxidizing cyclohexane with molecular oxygen or gases containing molecular oxygen in the liquid phase at from 130° to 200° C. and under pressure of from 5 to 25 bars, by treatment with aqueous solutions of an alkali metal hydroxide and/or alkali metal carbonate in two stages, the fresh aqueous alkali metal hydroxide and/or alkali metal carbonate solution being fed to the second stage and the separated-off spent alkali being brought into contact with fresh reaction mixture in the first stage.

The oxidation of cyclohexane with molecular oxygen produces, alongside cyclohexanol and cyclohexanone, acidic and other by-products which must be separated from the reaction mixture, or be decomposed, before isolating the valuable products. According to the process described in German Pat. No. 1,046,610, the reaction mixture containing cyclohexanol and cyclohexanone is first washed with water in order to remove the greater part of the acid constituents, and the reaction mixture thus obtained is then treated with sodium hydroxide solution in order to bind the remaining acid constituents and to split other by-products. However, in industrial production this produces substantial amounts of alkaline effluent which must be disposed of. Attempts have therefore been made to reduce the consumption of alkali metal hydroxide solution substantially.

Netherlands Patent Application 70/04,497 discloses a process in which reaction mixtures containing cyclohexanol and cyclohexanone are treated in two stages with an alkali metal hydroxide solution, the fresh alkali metal hydroxide solution being fed to the second stage and the spent alkali separated off in the second stage being brought into contact with fresh reaction mixture in the first stage. It is true that this procedure reduces the alkali consumption. However, in view of the great technical effort entailed in treating effluents there continues to be a need further to reduce the consumption of alkali metal hydroxide solution.

We have found that when working up reaction mixtures containing cyclohexanol and cyclohexanone, which have been obtained by oxidizing cyclohexane with molecular oxygen or gases containing molecular oxygen in the liquid phase at from 130° to 200° C. and under pressures of from 5 to 25 bars, by treatment with aqueous solutions of an alkali metal hydroxide and/or alkali metal carbonate in two stages, the fresh aqueous alkali metal hydroxide and/or alkali metal carbonate solution being fed to the second stage and the separated off spent alkali being brought into contact with fresh reaction mixture in the first stage, the process is more advantageous if the treatment in the first stage is carried out in the presence of inert gases and the inert gases are removed before the second stage.

The new process has the advantage that the consumption of alkali metal hydroxide solution is further reduced and hence the amount of effluent which requires purification is reduced.

The process starts from reaction mixtures which have been obtained by oxidizing cyclohexane with molecular oxygen or gases containing molecular oxygen, eg. air, at from 130° to 200° C. and under pressures of from 5 to 25 bars, in the presence or absence of catalysts. It is advantageous to wash the reaction mixtures thus obtained with water, before treating them further, in order to remove the greater part of the acid by-products. Typical reaction mixtures contain, in addition to cyclohexane, from 3 to 7 percent by weight of cyclohexanone and cyclohexanol and from 0.8 to 2.3 percent by weight of by-products such as acids and esters. For example, suitable reaction mixtures are obtained by the process described in German Pat. No 1,046,610.

The reaction mixture is treated, in two successive stages, with aqueous solutions of alkali metal hydroxide and/or alkali metal carbonate, the fresh aqueous alkali metal hydroxide and/or alkali metal carbonate solution being fed to the second stage and the separated-off spent alkali being brought into contact with fresh reaction mixture in the first stage. Each of the individual stages can be subdivided into several, eg. two or three, substages.

The use of aqueous solutions of sodium hydroxide or potassium hydroxide, or of the corresponding carbonates, is preferred. Because of their industrial availability, sodium hydroxide and sodium carbonate are particularly preferred. It is advantageous to use aqueous solutions of from 5 to 50 percent strength by weight, especially from 20 to 30 percent strength by weight. As a rule, from 3 to 10 g of alkali metal hydroxide or alkali metal carbonate, in the form of an aqueous solution, are used per kg of reaction mixture.

In the first stage, fresh reaction mixture is treated with the aqueous phase separated off in the second stage, i.e., with the spent alkali from the said stage. Advantageously, the first stage is carried out at from 100° to 150° C., especially from 110° to 140° C.

The treatment in the first stage is advantageously carried out at a pH of from 6 to 9.5, especially from 7.5 to 8.5. It has proved advantageous to use a residence time of from 1 to 10 minutes in the first stage.

It is an essential feature of the invention that the treatment in the first stage is carried out in the presence of inert gases. Examples of suitable inert gases are nitrogen or waste gases consisting essentially of nitrogen and containing less than 5 percent by volume of oxygen. It has proved particularly advantageous to use off-gas from the cyclohexane oxidation, which contains up to 3 percent by volume of oxygen, as the inert gas in the first treatment stage. Advantageously, from 5 to 50 liters (S.T.P.), especially from 10 to 30 liters (S.T.P.), of inert gases are used per kg of reaction mixture. The treatment in the first stage is advantageously carried out under a pressure of from 7 to 25 bars.

After the treatment in the first stage, the aqueous phase is separated off, for example in a separator, the aqueous phase being disposed of and the organic phase being passed to the second stage. It is essential that after the first stage the inert gases also used are also separated off, for example in the separator, and do not reach the second stage.

The organic phase from the first stage is treated in the second stage with freshly supplied aqueous alkali metal hydroxide and/or alkali metal carbonate solution, advantageously at from 100° to 150° C., especially from 110° to 140° C. The pressures as a rule vary from the vapor pressure of the reaction mixture at the particular temperature to 25 bars; the pH during the treatment is preferably 13.5 or above. It has also proved advantageous to employ residence times of from 3 to 20 minutes. After the treatment the mixture is separated into an organic phase and an aqueous phase by decanting, for example in a separator. The aqueous phase is passed, as spent alkali, to the first stage, whilst the organic phase is either fed to a further oxidation stage or is worked up, for example by distillation, cyclohexanone and cyclohexanol being obtained.

The consumption of alkali metal hydroxide and/or alkali metal carbonate can advantageously be reduced even further if heavy metal compounds are added to the reaction mixture containing cyclohexanol and cyclohexanone. Preferably, these are added in the first stage or even before the mixture enters the first stage.

Examples of suitable heavy metals are cobalt, nickel, molybdenum, chromium, manganese, vanadium and iron. Cobalt compounds are particularly preferred.

Usually, heavy metal compounds which are soluble in the cyclohexane, eg. the hexanoates or naphthenates, are used. However, it is advantageous if heavy metal compounds which are also not precipitated by water are used, for example complex compounds of cobalt, such as salicylaldehyde-amine complexes ("salcomines"). Cobalt compounds which on the one hand are soluble in the cyclohexane and on the other hand are derived from strong acids, i.e., acids with an activity comparable to phosphoric acid or sulfuric acid, have proved particularly suitable. Hence, the anions used are in particular those of phosphoric acid monoalkyl esters, phosphoric acid dialkyl esters, sulfuric acid monoalkyl esters, alkylsulfonic acids, alkylphosphonic acids and dialkylphosphinic acids. Instead of the alkyl compounds, the corresponding aralkyl compounds may also be used. In order to be able to utilize the oil-solubility of the compounds it is advantageous to use the anions of strong acids which contain a substituent of fairly long chain length, i.e., a substituent which confers solubility in the cycloalkane. Suitable alkyl compounds and esters are therefore especially those which contain an alkyl radical of 8 to 20 carbon atoms. Examples of such anions are those of phosphoric acid monooctyl ester, phosphoric acid monododecyl ester, phosphoric acid monolauryl ester, phosphoric acid dioctyl ester, phosphoric acid didodecyl ester, phosphoric acid dilauryl ester, sulfuric acid monooctyl ester, sulfuric acid monododecyl ester, sulfuric acid monolauryl ester, octylsulfonic acid, dodecylsulfonic acid, octylphosphonic acid, dioctylphosphinic acid, dodecylphosphonic acid or didodecylphosphinic acid. Examples of araliphatic derivatives are the anions of octylbenzenesulfonic acid and of dodecylbenzenesulfonic acid. In general, from about 0.1 to 10 ppm, especially from 0.2 to 0.5 ppm (by weight) of metal, based on the reaction mixture containing cyclohexanol and cyclohexanone, is used.

According to an industrial embodiment of the process which has proved particularly suitable, the said heavy metal compounds are additionally supplied to the second stage. They may be added to the organic phase from the first stage or to the fresh alkali metal hydroxide and/or carbonate solution. The heavy metal is as a rule used in an amount of from 0.01 to 10 ppm, calculated as metal and based on the reaction mixture containing cyclohexanol and cyclohexanone.

The process according to the invention is carried out, for example, as illustrated in the accompanying drawing. Fresh reaction mixture is fed in through line 1 and off-gas from the cyclohexane oxidation, in the stated amounts, is fed in through line 10, and spent alkali, from the separator 8, through line 2. The components are advantageously mixed in a mixing zone. The mixture is advantageously passed, under conditions corresponding to the stated residence times, into a separator 3, where the phases separate. The fully spent alkali is removed, for disposal, through line 4 and the inert gas which has been used is removed through line 11. The organic phase is passed through line 5 to the treatment vessel 7, fresh alkali metal hydroxide and/or alkali metal carbonate solution, in the stated concentration, being fed in, through line 6, whilst the mixture is still in the feed line 5. The reaction mixture is treated with the fresh alkali metal hydroxide and/or alkali metal carbonate solution in the vessel 7, advantageously for the stated residence time and at the stated temperatures, and is then passed through line 12 into the separator 8. There, the phases are separated, the aqueous phase being recycled, as spent alkali, into line 1 through line 2, whilst the treated reaction mixture is discharged through line 9. Catalyst may, if required, be added through line 13.

Cyclohexanol and cyclohexanone are used for the manufacture of adipic acid or caprolactam.

The process of the invention is illustrated by the examples which follow.

EXAMPLE 1

Per hour, 148 kg of a reaction mixture which has been washed with water and which contains, in addition to cyclohexane, 7.79 kg of cyclohexanone and cyclohexanol and 1.59 kg of by-products, eg. acids and esters, are fed through line 1 into an apparatus as shown in the drawing. Per hour, 3.3 cubic meters (S.T.P.) of off-gas from the cyclohexane oxidation are fed in, under a pressure of 11 bars, through line 10. In addition to nitrogen, the off-gas contains up to 0.3 percent by volume of oxygen, 1.2 percent by volume of CO and 1.2 percent by volume of $CO_2$, and is saturated with cyclohexane. At the same time, 1.8 l/hr of the spent alkali from the separator 8 are fed in through line 2. The mixture is passed into the separator 3° at 125° C. The off-gas is removed through line 11 and the aqueous spent alkali is removed through line 4. The pH of the aqueous phase is 8.2. The organic phase is removed through line 5 and, per hour, 0.51 kg of sodium hydroxide in the form of 25 percent strength aqueous solution is fed in through line 6. The mixture thus obtained is treated for 5 minutes in the treatment vessel 7 at 125° C. and a pH of >14 and is passed through line 11 into the separator 8. In the separator 8, the mixture is separated, the aqueous spent alkali being recycled through line 2, whilst the treated reaction mixture is removed through line 9. Per kg of cyclohexanol and cyclohexanone produced, 0.26 kg of 25 percent strength by weight aqueous sodium hydroxide solution is consumed. The completely spent alkali produced, as removed through line 4, contains no free sodium hydroxide.

COMPARATIVE EXAMPLE

The procedure described in Example 1 is followed, except that no off-gas is fed in through line 10. 2.4 kg of a 25 percent strength by weight aqueous sodium hydroxide solution have to be fed in through line 6. Per kg of cyclohexanol and cyclohexanone, the consumption of 25 percent strength by weight aqueous sodium hydroxide solution is 0.30 kg.

If the treatment with sodium hydroxide solution is carried out in one stage in the absence of the inert gas, 0.42 kg of aqueous sodium hydroxide solution is required per kg of cyclohexanone and cyclohexanol. The spent alkali formed still contains 4% of free sodium hydroxide.

EXAMPLE 2

If the procedure described in Example 1 is followed but 15 g/hr of 1 percent strength catalyst solution are fed in through line 13, the required amount of sodium hydroxide solution is reduced to 0.20 kg of 25 percent strength by weight aqueous sodium hydroxide solution per kg of cyclohexanol and cyclohexanone produced.

We claim:

1. In a process for working up reaction mixtures containing cyclohexanol and cyclohexanone, which have been obtained by oxidizing cyclohexane with molecular oxygen or gases containing molecular oxygen, in the liquid phase, at from 130° to 200° C. under a pressure of from 5 to 25 bars, working-up being effected by treatment with aqueous solution of an alkali metal hydroxide and/or alkali metal carbonate in two stages, the fresh aqueous alkali metal hydroxide and/or alkali metal carbonate solution being fed to the second stage and the separated-off spent alkali being brought into contact with fresh reaction mixture in the first stage, the improvement of carrying out the treatment in the first stage in the presence of inert gases and separating off the inert gases before the second stage.

2. A process of claim 1, in which from 5 to 50 liters (S.T.P.) of inert gas per kg of reaction mixture are also used in the first stage.

3. A process of claim 1, in which off-gas from the cyclohexane oxidation is used as the inert gas.

4. A process of claim 1, in which a pressure of from 7 to 25 bars is maintained in the first stage.

5. A process as claimed in claim 1, in which a pH of from 6 to 9.5 is maintained in the first stage and a pH of 13.5 or above is maintained in the second stage.

6. A process of claim 1, in which a temperature of from 110° to 140° C. is maintained in stages 1 and 2.

7. A process of claim 1, in which a residence time of from 1 to 10 minutes is maintained in the first stage and a residence time of from 3 to 20 minutes is maintained in the second stage.

8. A process of claim 1, in which heavy metal compounds are used additionally.

9. A process of claim 1, in which heavy metal compounds are added in the first and second stages.

* * * * *